Goldstein et al.

United States Patent [19]

[11] Patent Number: 4,931,445
[45] Date of Patent: Jun. 5, 1990

[54] AGENTS FOR TREATMENT OF MALE IMPOTENCE

[76] Inventors: Irwin Goldstein, 85 Old Farm Rd., Milton, Mass. 02187; Inigo S. de Tejada, 82 Willet St., Wollaston, Mass. 02170; Leslie A. Riblet, 145 Chestnut Hill Rd., Killingworth, Conn. 06417

[21] Appl. No.: 254,346

[22] Filed: Oct. 6, 1988

[51] Int. Cl.$^5$ .............................................. A61K 31/50
[52] U.S. Cl. ................................................... 514/252
[58] Field of Search ......................................... 514/252

[56] References Cited

U.S. PATENT DOCUMENTS

| | | | |
|---|---|---|---|
| 3,857,845 | 12/1974 | Palazzo | 260/268 PH |
| 4,127,118 | 11/1978 | Latorre | 128/79 |
| 4,132,791 | 1/1979 | Silvestrini | 424/250 |
| 4,162,318 | 7/1979 | Silvestrini | 424/250 |
| 4,687,771 | 8/1987 | Gamble et al. | 514/253 |

OTHER PUBLICATIONS

"USAN and the USP Dictionary of Drug Names" 1988 Edn., p. 217 (1/11).
Lisciani, et al., Arzneim. Forsch/Drug Research (1978) 28 (II), pp. 417–423 (1/19).
L. M. Martin, *Geriatrics* (12/80) pp. 79–83 (2/12).
H. G. Kudish, *Postgraduate Medicine,* vol. 74/4 (10/83) pp. 233–240 (2/23).

*Primary Examiner*—Leonard Schenkman
*Attorney, Agent, or Firm*—Richard P. Ryan

[57] ABSTRACT

Etoperidone and its pharmaceutically acceptable salts are useful in the treatment of male sexual impotence.

8 Claims, No Drawings

AGENTS FOR TREATMENT OF MALE IMPOTENCE

FIELD OF THE INVENTION

This invention is concerned with a drug bio-affecting body-treating process which employs 2-[3-[4-(3-chlorophenyl)-1-piperazinyl]propyl]-4,5-diethyl-1,2,4-triazol-3-one or pharmaceutically acceptable acid addition salts thereof.

BACKGROUND OF THE INVENTION

The pharmacologic agent utilized in the method of the instant invention is 2-[3-[4-(3-chlorophenyl)-1-piperazinyl]-propyl]-4,5-diethyl-1,2,4-triazol-3-one, also known as etoperidone ("USAN and the USP Dictionary of Drug Names", 1988 Edition; M. C. Griffith, Editor, U.S. Pharmacopeial Convention, Inc., Mack Printing Co., Easton, Pa., page 217).

Etoperidone has been disclosed as having hypotensive and analgesic activities (Palazzo; U.S. Pat. No. 3,857,845) and as being of use in treating Parkinsonism and other extra-pyramidal syndromes characterized by tremors (Silvestrini; U.S. Pat. Nos. 4,132,791; 4,162,318). The pharmacology of etoperidone has been extensively detailed by Lisciani, et. al., *Arzneim. Forsch/Drug Research* (1978) 28 (II), pp. 417–423.

Pertaining to the use envisioned in the instant invention, the antidepressant drug, 2-[3-[4-(3-chlorophenyl)-1-piperazinyl]-propyl]-1,2,4-triazolo[4,3-a]pyridin-3(2H)-one (also known as trazodone) and its salts have been disclosed as being useful in treating male impotence (Gamble, et al., U.S. Pat. No. 4,687,771 and pending application U.S. Ser. No. 070,851). Direct penile injection of certain vasodilators and/or adrenergic blocking agents for the purpose of causing penile erections has also been disclosed (Latorre; U.S. Pat. No. 4,127,118). Currently, yohimbine is being studied for possible use in the treatment of impotence.

Male impotence is a sexual dysfunction which relates to difficulty in achieving and/or maintaining penile erection sufficiently rigid for satisfactory coitus. Currently, male impotence is a broad-ranging problem of social, psychologic, and medical significance. There exists today a diversity of possible causes of impotence as well as suggested methods of treatment. These have been described in a number of available literature reviews on male impotence and on male sexual dysfunctioning in general. While impotence can result from psychogenic or physical causes, a review by L. M. Martin in *Geriatrics*, (December 1980), pages 79–83; emphasizes that organic causes of impotence are more common than has been currently believed. Any condition that impairs the endocrine, vascular, neurologic, or anatomic systems that pertains to the erectile mechanism can produce impotence. The various causes of impotence that have been specifically implicated are: diabetes, radical pelvic surgery, peripheral vascular disease, hypertension and hardening of arteries, side-effects from drugs, and hormonal imbalance.

Concerning the treatment of impotence, H. G. Kudish in *Postgraduate Medicine*, Vol. 74/4 (October 1983), pages 233–240; lists therapies for impotence as being in two categories: surgical and non-surgical. The surgical category comprises implantation of a penile prosthetic device; revascularization of the arteries of the penis; ligation/excision of the veins draining the penis and incision or excision of Peyronie's plaques. The non-surgical category comprises sex therapy, endocrine therapy, pharmacologic therapy, and electrostimulation. Non-surgical therapies, when effective, are the treatments of choice. Of these, the favored treatment in most instances would be oral pharmacologic therapy if it was effective. Unfortunately, the use of oral pharmacologic agents in the treatment of impotence has achieved little success. This is evidenced by the absence of any widely accepted oral pharmacologic treatment for use in male impotence. Although anecdotal reports regarding various agents, compositions, and formulations to be employed for this purpose abound.

Considering the present state of the art, there exists nothing in the prior art which teaches or suggests that etoperidone would be useful in the treatment of impotence in males with compromised penile erection function.

SUMMARY AND DETAILED DESCRIPTION

Erectile impotence has been defined by Masters and Johnson (W. H. Masters, V. E. Johnson; *Human Sexual Inadequacy*, Little, Brown and Company, Boston, 1970, page 157) as the "inability to achieve or maintain an erection [of] quality sufficient to accomplish successful coital connection". Since erectile impotence can result from a variety of underlying causes ranging from purely psychogenic to completely physical dysfunctioning, it would be unrealistic to expect a single treatment modality to be effective in all cases. In current medical practice, impotence is treated by determining the underlying cause or causes and then treating them whenever possible. When irreversible organic impotence is found, however, penile prosthesis implantation is considered the most beneficial and statistically successful treatment. For psychogenic causes of impotence, the underlying condition is treated with psychopharmacologic agents and/or behavioral therapies. In some cases, identification of the underlying causes of male impotence cannot be determined with certainty.

An object of the present invention then is to produce an effective male erection in those subpopulations of impotent males where the underlying causes of impotence are amenable to pharmacologic intervention of this sort.

The process of the present invention is intended for treatment of male impotence. The process essentially involves administration of etoperidone or a pharmaceutically acceptable acid addition salt thereof, to a male mammal in need of such treatment. The effectiveness of etoperidone in the induction of penile erections was determined in an in vivo animal model. Intercavernosal injection of etoperidone hydrochloride induced rigid erections in the test animals at doses from 0.25 to 4 mg with duration of erection effect indicating dose-dependence. The etoperidone-induced prolonged penile erection could be readily brought to the flaccid state by intracavernosal injection or irrigation with phenylephrine.

Administration of etoperidone according to the present invention may be made by the parenteral, oral or rectal routes. Although oral administration of etoperidone is a preferred route of administration, being both effective and harmless for most patients, nonetheless a parenteral method of administration, direct injection into the penis, is the most preferred route of administration for practice of the method of this invention. For certain patients that may experience unreliable penile erectile responses and/or potential side effects with oral dosing of etoperidone direct administration of the drug into the penis itself represents a useful option in treating male impotence.

For use in the instant process oral administration of etoperidone hydrochloride from about 50 to 400 mg per day is anticipated as being the preferred dosage regimen. Dosage adjustment is to be made depending on the response seen in each individual. It is recommended that etoperidone be given accompanied by some food and starting at the level of 50 mg per day. Preferably, the drug should be taken at bedtime. The drug may then be increased by 50 mg increments, as tolerated, every 3 to 7 days. As the total dosage increases, the drug may be administered in divided doses. No more than 300 mg of etoperidone is to be given as a single dose. Male patients being treated with etoperidone for impotence should be monitored carefully by their attending physician during the dose-titration period of treatment. Since the dosage should be tailored to the individual patient, it is suggested that one commence with a dose of about 50 mg per day administered at bedtime and then increase the dose every 3 to 7 days by 50 mg at each dosage time until the desired response is observed or until the patient exhibits side effects. Administration of the daily dosage in divided doses may be recommended in some instances. The emergence of side effects such as dizziness, drowsiness, or prolonged or inappropriate penile erection serves as indication to the attending physician or health specialist that a discontinuation or reduction in the amount of etoperidone administered would be appropriate.

The direct penile administration of etoperidone encompasses introduction of the drug substance into erectile tissues of the penis, the corpora cavernosa, so that an erection of the penis is effected and/or enhanced and this resultant erection maintained for a satisfactory time period. While direct introduction of etoperidone into penile erectile tissue is preferably by injection, subcutaneous and transdermal administration techniques are also intended. It is also to be understood that the penile injections may be multiple. For direct penile administration of etoperidone, lower doses are of course employed than those given when the oral route of administration is selected. For purposes of the direct penile administration aspect of the present invention, dose levels of from about 1 to 10 mg, preferably 2 to 8 mg, etoperidone would represent the recommended dose levels.

EXPERIMENTAL

Rabbit Model: Penile Erection Induction

The New Zealand White rabbit was anesthetized by the intravenous injection of sodium pentobarbital in a 1:1 solution with sterile saline. A dorsal incision in the prepuce was performed to expose the glans penis and the right and left corporal bodies. A 21 gauge butterfly needle was inserted in one corporal body for injection of etoperidone hydrochloride and for saline irrigation of the corporal bodies. A second 21 gauge butterfly was introduced into the contralateral corporal body and connected to a pressure transducer via heparinized saline-filled pressure tubing to record on-line corporal body pressure. A 20 gauge angiocatheter was placed in one carotid artery to record systemic arterial blood pressure.

Etoperidone hydrochloride was placed into solution so that for different concentrations the volume administered was consistently 0.5 ml. This volume is approximately 20–30% of the total volume of the corpora cavernosa in the rabbit.

Any increase in corporal body pressure was recorded and compared to the systemic arterial blood pressure. A rigid erection was considered to exist when the corporal body pressure equilibrated at a pressure value equal to or within 10% of the mean systemic diastolic blood pressure.

What is claimed is:

1. A method for treating male sexual impotence which comprises administering a non-toxic therapeutically effective dose of etoperidone or a pharmaceutically acceptable acid addition salt thereof to a patient in need of such treatment.

2. The method of claim 1 wherein etoperidone hydrochloride is employed and dosage is by the oral route.

3. The method of claim 2 wherein said patient is an adult and a daily dose of from about 50 mg to 400 mg is employed.

4. The method of claim 3 wherein said daily dose is divided and administered b.i.d.

5. The method of claim 3 wherein said daily dose is divided and administered t.i.d.

6. The method of claim 1 wherein etoperidone hydrochloride is employed and is administered directly to the penis.

7. The method of claim 6 wherein the administration is by injection into penile erectile tissue.

8. The method of claim 6 wherein the dose is from about 2 to 8 mg of etoperidone hydrochloride.

* * * * *